United States Patent [19]

Tetreault

[11] Patent Number: 5,247,972

[45] Date of Patent: Sep. 28, 1993

[54] ALIGNMENT GUIDE FOR HYPODERMIC SYRINGE

[75] Inventor: Emery J. Tetreault, Pepperell, Mass.

[73] Assignee: Whittier Medical, Inc., Still River, Mass.

[21] Appl. No.: 808,755

[22] Filed: Dec. 17, 1991

[51] Int. Cl.$^5$ .......................... B65B 3/04; A61H 5/00
[52] U.S. Cl. .................................... 141/27; 141/97; 141/383; 141/386; 604/411; 604/414; 604/905; 604/187
[58] Field of Search ................ 141/27, 28, 21, 26, 141/25, 97, 383, 386; 604/414, 411, 187, 193, 207, 905

[56] References Cited

U.S. PATENT DOCUMENTS

| | | | |
|---|---|---|---|
| D. 280,018 | 8/1985 | Scott | D24/25 |
| 3,833,030 | 9/1974 | Waldbauer, Jr. et al. | 141/26 |
| 3,844,318 | 10/1974 | Raia et al. | 141/27 |
| 3,875,979 | 4/1975 | Hults | 141/27 |
| 3,965,945 | 6/1976 | Ross | 141/27 |
| 4,219,055 | 8/1980 | Wright | 141/27 |
| 4,475,915 | 10/1984 | Sloane | 604/414 |
| 4,623,344 | 11/1986 | Eriksson | 604/407 |
| 4,747,834 | 5/1988 | Prindle | 604/184 |
| 4,872,494 | 10/1989 | Coccia | 141/383 |

OTHER PUBLICATIONS

Design News, Oct. 23, 1989, p. 53.

Primary Examiner—Ernest G. Cusick
Attorney, Agent, or Firm—Wolf, Greenfield & Sacks

[57] ABSTRACT

An alignment guide for hypodermic syringes for facilitating the withdrawal of fluid samples from one or more bottles. The guide assures perpendicular puncturing of a serum bottle septum and provides for easy disassembly for cleaning. The syringe alignment guide includes an inner tube concentrically disposed inside of a tubular housing. The inner tube has first and second ends, and an internal bore for receiving a hypodermic syringe barrel. The first end of the inner tube includes a means for mounting a hypodermic syringe and a means for removably securing the inner tube within the tubular housing. The second end of the inner tube includes a means for mounting a fluid-containing bottle which extends co-axially from the second end of the inner tube and comprises a plurality of protrusions.

7 Claims, 2 Drawing Sheets

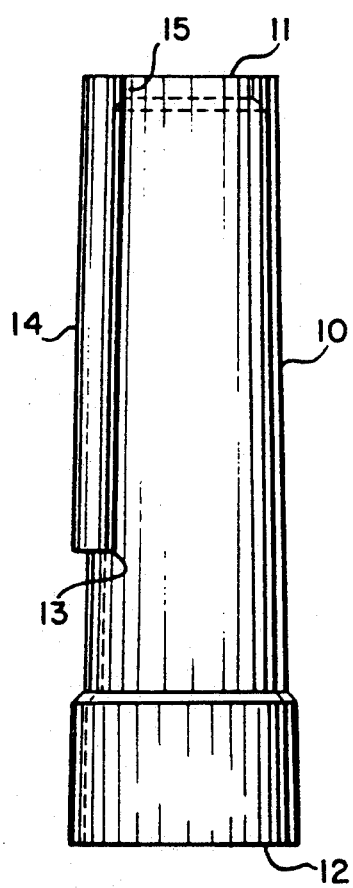
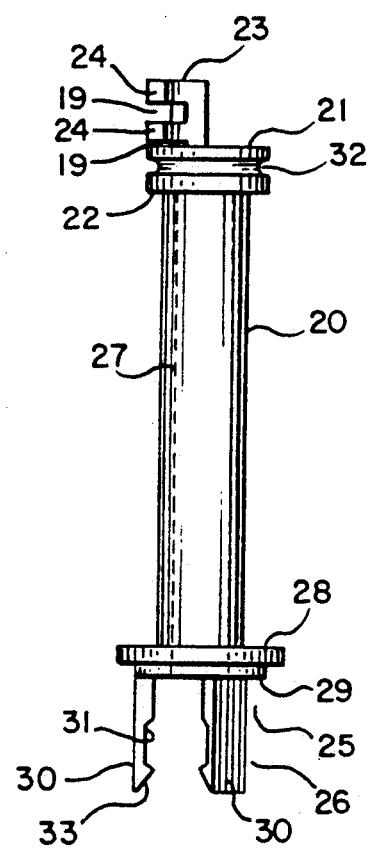
Fig. 1A
Fig. 1B

ALIGNMENT GUIDE FOR HYPODERMIC SYRINGE

BACKGROUND OF THE INVENTION

1. Field of the Invention

The present invention relates to an alignment guide for hypodermic syringes.

2. Description of the Prior Art

Injectible medications, pharmaceuticals and other suspensions are typically stored in fluid-containing serum bottles that have an elastomeric seal or septum through which a hypodermic syringe needle is introduced.

Conventional methods for withdrawing a measured volume of liquid from a serum bottle involve holding the bottle with the fingers of one hand and inserting the needle attached to a hypodermic syringe through the septum by holding the syringe with the other hand. In the case of self-administered medicaments, such as insulin, where the patient may have a limited supply of extra needles, the needle should penetrate the septum at a right angle in order to avoid possibly bending the needle against an inside wall of the serum bottle. For patients who are aged or infirm, the entire manipulative procedure may be difficult. Moreover, certain medical procedures require the injection of a plurality of liquid medicaments from several bottles. Rather than requiring a patient to self-administer a plurality of injections which can be a painful and difficult process, it would be useful to provide a means for easily introducing more than one type of liquid into a single syringe.

While various syringe guides have been available in the prior art, these guides have lacked positive positioning of the serum bottle to assure right angle puncturing of the septum, whether the syringe is inserted into the guide holding the bottle or a new bottle is inserted into the guide holding the syringe. Such guides have also lacked easy locking of the syringe in the guide and easy disassembly of the syringe for cleaning, as required by government (Food and Drug Administration) regulations.

It is therefore an object of this invention to provide an improved syringe guide. Other objects of the invention are to provide a syringe guide with positive positioning for the serum bottle, which can be easily assembled and disassembled.

SUMMARY OF THE INVENTION

According to the present invention, a syringe alignment guide comprises two primary parts: a tubular housing and an inner tube. The inner tube has a first and second end, and an internal bore for receiving a hypodermic syringe barrel. The first end of the inner tube includes a means for mounting a hypodermic syringe barrel. The second end of the inner tube includes a means for mounting a fluid-containing bottle.

In its assembled configuration, the syringe alignment guide of the present invention comprises an inner tube concentrically disposed inside of a tubular housing. The inner tube has a first and second end, and an internal bore for receiving a hypodermic syringe barrel. The first end of the inner tube includes a means for mounting a hypodermic syringe barrel and a means for securely mounting the inner tube within the tubular housing, that protrude from the first end of the tubular housing. The second end of the inner tube includes a means for mounting a fluid-containing bottle.

Once the syringe alignment guide of the present invention is in its assembled configuration, a fluid-containing bottle and a hypodermic syringe may be mounted therein. The fluid-containing bottle may be easily detached from the means for mounting the bottle. Therefore, a plurality of fluids may be withdrawn from a series of bottles into a single syringe mounted on the apparatus. The process for providing a plurality of different fluids to a single syringe includes the steps of mounting a hypodermic syringe by inserting it in the first end of the inner tube and into the bore, rotating the syringe barrel so that the barrel flange is locked in the syringe mounting means, and mounting a fluid-containing bottle by pressing the bottle cap into snap-fit engagement with the bottle mounting means. The syringe needle penetrates the bottle through the elastomeric septum located within the bottle cap, and the first fluid is withdrawn into the syringe barrel. The first bottle can then be replaced with a second bottle of the same or different fluid, and because the syringe is aligned in the inner tube, the needle will penetrate the septum of the second bottle in the same manner as the first bottle.

Thus, the present invention provides an alignment guide for hypodermic syringes. Moreover, the guide facilitates the withdrawal of fluid samples from a plurality of bottles. The present invention is particularly advantageous for self-administration of these medicaments since only one hand is needed to operate the unit which accommodates both the hypodermic syringe and the bottle. The present invention also assures perpendicular puncturing of the septum, whether the syringe is inserted into the guide holding the bottle or a new bottle is inserted into the guide holding the syringe. The guide of the present invention also provides for easy disassembly for cleaning, as required by government regulations.

Other objects and features of the present invention will become apparent from the following detailed description when taken in connection with the accompanying drawings which disclose a preferred embodiment of the invention. It is to be understood that the drawings are designed for the purpose of illustration only and are not intended as a definition of the limits of the invention.

BRIEF DESCRIPTION OF THE DRAWINGS

The foregoing and other objects and advantages of the invention will be appreciated more fully from the following drawings in which:

FIGS. 1A and 1B are side views of the tubular housing and the inner tube respectively of a preferred embodiment of the present invention;

DETAILED DESCRIPTION OF THE INVENTION

Figure 2:
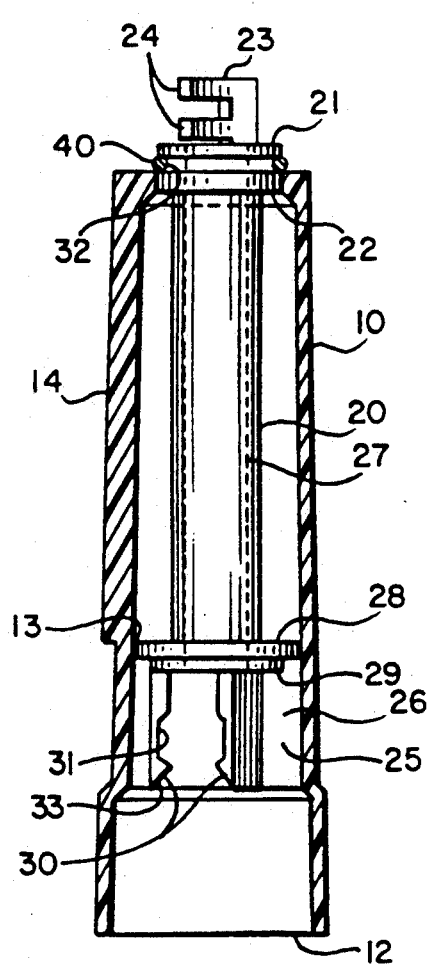
FIG. 2 is a side view of the components of FIGS. 1A and 1B in assembled form.

Turning now to the Figures, FIGS. 1A and 1B, show side views of a tubular housing 10 and a inner tube 20, respectively, for a preferred embodiment of the present invention. The tubular housing 10 has a first end 11 and a second end 12. Typically, housing 10 is cylindrical and is slightly tapered toward the first end 11 to accommodate inner tube 20. However, housing 10 may also be cylindrical throughout its entire length, or tapered toward its second end 12 to accommodate various sized inner tubes 20. Preferably, a shoulder 13 is provided on the inside surface of housing 10 to limit the insertion of inner tube 20. Other means may also be used to limit the insertion of the inner tube 20 as would be apparent to those of skill in the art.

The housing 10 is typically made of a clear plastic or glass material to allow the user to accurately measure the volume of liquid withdrawn from a serum bottle. In a preferred embodiment of the present invention, there is a magnifying lens 14 integral with the outer surface of housing 10 to enhance visualization and thereby allow for more precise withdrawal of specific volumes of liquid.

Inner tube 20 terminates at first end 21 in a flange 22, from which an element 23 for mounting a hypodermic syringe extends. Typically, the element 23 for mounting a hypodermic syringe protrudes from the periphery of the flange 22, and has a plurality of substantially orthogonal projections 24 with grooves 19 therebetween in which a flange of a hypodermic syringe may be fitted in a manner to be described later. Flange 22, which has a groove 32 extending around its outer surface, coacts with shoulders 15 to support the inner tube in housing 10 at the first end when assembled.

Second end 25 of inner tube 20 terminates in a retaining ring 28 and an adjacent flange 29. Extending from flange 29 is a mounting assembly 26 for a fluid-containing bottle. For the preferred embodiment, assembly 26 extends co-axially from the periphery of the flange 29, and has a plurality of finger-like protrusions 30 disposed around the outer surface of the flange. Preferably, there are three protrusions 30 to securely mount a fluid-containing bottle. The inner surface of the protrusions 30 have beveled tips 33 and indentations 31 to better engage a fluid-containing bottle and accommodate a bottle cap. The lower edge of the indentations 31 are slightly beveled to facilitate bottle release.

Typically, the inner tube 20 is cylindrical and has an annular bore 27 along its entire length. The inner tube 20 is also typically made of a clear plastic to allow the user to view the syringe barrel and thus to accurately measure the volume of fluid withdrawn from a serum bottle.

Turning now to FIG. 2, the syringe alignment guide of the present invention is shown in its assembled configuration. Inner tube 20 is concentrically disposed inside housing 10. The two parts are assembled by inserting the first end 21 of inner tube 20 into the second end 12 of housing 10 until retaining ring 28 on the second end 25 of inner tube 20 engages with the shoulder 13 on the inside surface of housing 10. This limits further movement of the inner tube 20 and allows a portion of the first end 21 of inner tube 20 to protrude from the first end 11 of housing 10. The projecting first end portion of inner tube 20 includes mounting element 23 and a portion of flange 22 includinq groove 32. The portion of flange 22 below groove 32 engages shoulder 15 to align the first ends of tubes 10 and 20. Groove 32 is designed to engage and have seated therein an elastomeric O-ring 40 or similar device, which also overlaps the top portion of the first end 11 of housing 10. By positioning the O-ring 40 over element 23 and over the upper portion of flange 22 into groove 32, inner tube 20 is securely mounted within tubular housing 10. Once assembled, inner tube 20 and housing 10 are axially rotatable relative to one another to allow magnifying lens 14 to be aligned with markings on a hypodermic syringe barrel (not shown). By removing the O-ring 40, the inner tube 20 can be easily withdrawn for cleaning.

The remainder of inner tube 20 is enclosed within housing 10, including assembly 26 for mounting a fluid-containing bottle.

Figure 3:
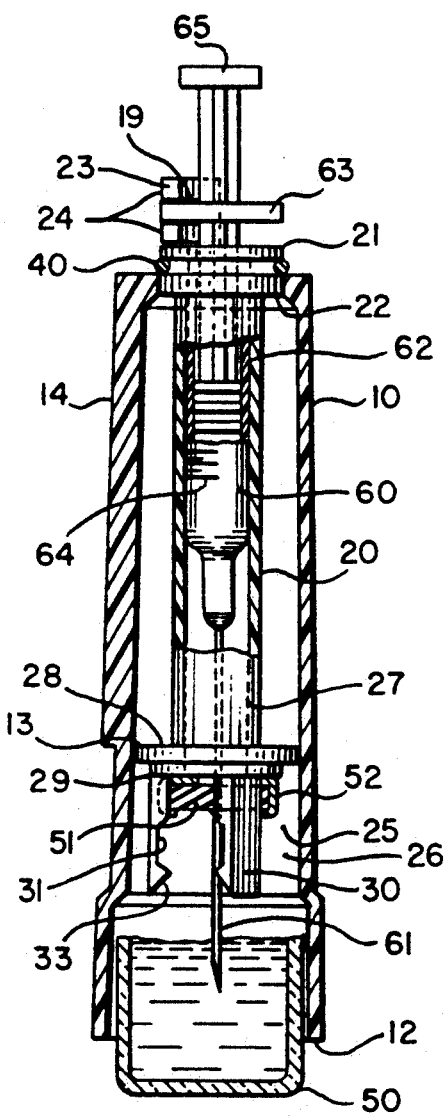
FIG. 3 is a side view of the assembly of FIG. 2 in use with a hypodermic syringe and a fluid-containing bottle mounted therein.

Referring now to FIG. 3, the syringe alignment guide of the present invention is shown assembled with a fluid-containing bottle 50 and a hypodermic syringe 60 mounted therein. Inner tube 20 and tubular housing 10 may be assembled as described above.

Bottle 50 may be any conventional serum bottle, such as an insulin bottle. Typically the fluid-containing bottle 50 has an elastomeric septum 51 disposed within the bottle cap 52. The septum 51 is designed to be perpendicularly punctured by a hypodermic syringe needle. The hypodermic syringe 60 is also a conventional or disposable syringe, that includes a needle 61 engaged with a syringe barrel 62 by way of typical fittings. The syringe barrel 62 typically has a syringe barrel flange 63 opposite the needle 61 and a plunger 65 within the barrel and extending therefrom.

In operation, the hypodermic syringe 60 with needle 61 is inserted at the first end 21 of inner tube 20 into the annular bore 27. The syringe barrel 62 is then rotated so that the barrel flange 63 is engaged in a groove 19 between two of the projections 24 on syringe mounting element 23. The grooves 19 formed by the projections 24 allow various sized syringes to be mounted. Either before or after the mounting of the syringe, fluid-containing bottle 50 is enqaged in the second end 25 of inner tube 20 by pressing the bottle cap 52 of bottle 50 into snap-fit engagement with the projections 30 of assembly 26. As the later mounted of the syringe and bottle is being brought into position, syringe needle 61 penetrates bottle 50 through elastomeric septum 51. The straight bore 27 of inner tube 20 will align the needle 61 of the hypodermic syringe 60 perpendicularly with the septum 51 of the bottle. Because the inner tube 20 and housing 10 are axially rotatable relative to one another, the magnifying lens 14 may be aligned with markings on the syringe barrel 64 to allow precise withdrawal of specific volumes of fluid.

Further, the fluid-containing bottle 50 may be easily detached from the mounting assembly 26. Therefore, the present invention may be used to introduce more than one type of fluid into syringe barrel 62. In this operation, once the first fluid is withdrawn from a first bottle 50 into syringe barrel 62, as described above, the first bottle can be replaced with a second bottle of the same or different fluid. Because syringe 60 and needle 61 are aligned and essentially immobile in inner tube 20, the syringe needle 61 will penetrate the septum 51 of the second bottle 50 in the same manner as the first bottle 50.

When use of the guide has been completed and the bottle and syringe are removed, O-ring 40 may be easily removed, a tab (not shown) being provided on the O-ring for this purpose, and the tubes 10 and 20 separated for cleaning. Since neither septum 51 nor needle 61 comes in contact with the guide, it need only be washed, for example in a home dishwasher, and need not be sterilized.

The foregoing detailed description has been given for clearness of understanding only, and unnecessary limitations are not to be construed therefrom. The invention is not to be limited to the exact details shown and described since obvious modifications will occur to those skilled in the art, and any departure from the description herein that conforms to the present invention is intended to be included within the scope of the claims.

What is claimed is:

1. A syringe alignment guide comprising:
   a tubular housing;
   an inner tube having an internal bore for receiving a hypodermic syringe, said inner tube having first and second ends;
   means for mounting a hypodermic syringe adjacent to the first end of the inner tube including a portion which protrudes from the periphery of the first end of the inner tube, said portion is parallel to the axis of the inner tube and has a plurality of projections orthogonally positioned relative to the protruding portion;
   means for mounting a fluid-containing bottle extending co-axially from the second end of the inner tube including a plurality of protrusions; and
   means for removably securing the inner tube within the tubular housing.

2. The syringe alignment guide of claim 1 wherein the means for mounting a fluid-containing bottle comprises three finger-like protrusions.

3. The syringe alignment guide of claim 1 wherein said tubular housing includes a magnifying lens integral with the outer surface of the housing.

4. A syringe alignment guide comprising:
   a tubular housing having a first end and a second end;
   an inner tube concentrically disposed in said tubular housing having an internal bore for receiving a hypodermic syringe, said inner tube having first and second ends;
   means for mounting a hypodermic syringe adjacent to the first end of the inner tube and protruding from the first end of the tubular housing;
   means for mounting a fluid-containing bottle extending co-axially from the second end of the inner tube including a plurality of protrusions; and
   means for removably securing the inner tube within the tubular housing including an elastomeric O-ring positioned around the outer surface of the first end of the inner tube and over the top portion of the first end of the tubular housing.

5. The syringe alignment guide of claim 4 wherein the inner tube and housing are axially rotatable relative to one another.

6. The syringe alignment guide of claim 4 wherein the means for mounting a fluid-containing bottle comprises three finger-like protrusions.

7. The syringe alignment guide of claim 4 wherein said tubular housing includes a magnifying lens integral with the outer surface of the housing.

* * * * *